United States Patent [19]

Okada et al.

[11] Patent Number: 4,962,225

[45] Date of Patent: Oct. 9, 1990

[54] ASPARTIC ACID DERIVATIVES

[75] Inventors: Yoshio Okada, Akashi; Koichi Kawasaki; Shin Iguchi, both of Kobe, all of Japan

[73] Assignee: Hidehiko Watanabe, Hiroshima, Japan

[21] Appl. No.: 176,597

[22] Filed: Apr. 1, 1988

[51] Int. Cl.⁵ .................................... C07C 125/065
[52] U.S. Cl. ................................ 560/163; 560/157; 560/162; 560/171

[58] Field of Search ................ 560/163, 162, 171, 157

*Primary Examiner*—Michael L. Shippen
*Attorney, Agent, or Firm*—Flehr, Hohbach, Test, Albritton & Herbert

[57] ABSTRACT

New aspartic acid derivatives include N-α-t-butoxycarbonyl-aspartic acid-β-2-adamantyl ester-α-benzyl ester, N-α-t-butoxycarbonyl-aspartic acid-β-2-adamantyl ester and benzyloxycarbonyl-aspartic acid-β-2-adamantyl ester-α-benzyl ester.

4 Claims, 1 Drawing Sheet

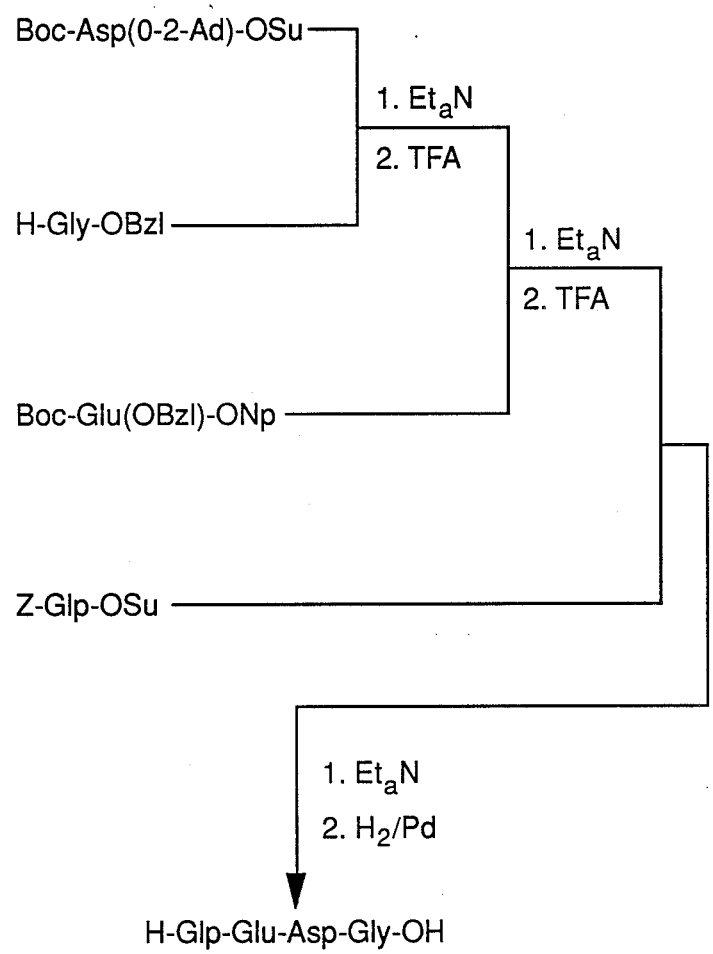

ASPARTIC ACID DERIVATIVES

BACKGROUND OF THE INVENTION

This invention relates to aspartic acid derivatives and their salts.

In peptide synthesis, ω-carboxyl groups or α-carboxyl groups must normally be protected. Regarding the protecting groups for the ω-carboxyl groups of dicarboxylamino acids (such as aspartic acid, glutamic acid, α-aminoadipic acid and α-aminopimetic acid), it is necessary to selectively cleave the α-carboxyl protecting groups of these amino acids. In the past, benzyl group which is stable against acids such as trifluoroacetic acid and can be removed by catalytic reduction or t-butyl group which is stable against catalytic reduction and can be removed with an acid was frequently used as a protecting group for ω-carboxyl group but several technological problems have been noted and there has been an increased demand for development of superior protecting groups.

More in detail, benzyl group has been frequently used as the protecting group for ω-carboxyl group in peptide synthesis but it is known that succinimide formation takes place during the condensation or deprotection reaction. If the peptides contain aspartyl-glycine or aspartyl-serine linkage, in particular, such side reactions become dominant and it is difficult to obtain a high yield of the target substance. This phenomenon was reported also in the case of glutamic acid, for example, by Battersby, et al. (J. Chem. Soc., pp. 259–269 (1955)) and Hanson, et al (ibid., pp. 836–842 (1964)). Use has also been made frequently of t-butyl group but it is difficult to introduce t-butyl group into carboxyl group and it can be applied industrially only to a limited extent (Katsoyannis, et al., "Methods In Enzymology", Vol. 47, Part E. "Enzyme Structure", pp. 529–532, Academic Press, New York (1977)). As for the hydrogen fluoride method which has conventionally been used as the method of final deprotection whereby all protecting groups are removed, it is recently pointed out that there are various problems of side reactions which are difficult to eliminate (B. Ridge, "Amino-Acids Peptides and Proteins", The Chemical Society, Vol. 6, p. 302 (1975)). Thus, methods with trifluoromethanesulfonic acid and methanesulfonic acid were proposed to take the place of the conventional hydrogen fluoride method and came to be used frequently (Yajima, et al., J.C.S. Chem. Comm., p. 107 (1974)). More recently, a method by the use of trimethylsilyl-trifluoro-methanesulfonate (Yajima, et al., J.C.S. Chem. Comm., pp. 274–275 (1987)) was proposed and not only has it become a generally accepted idea that the final deprotection be carried out under a milder acidic condition so as not to damage the peptide chain during the synthesis, if possible, but also a more strongly selective group which is stable against temporary deprotection of α-amino protecting group but removable under a milder acidic condition at the time of the final deprotection is desirable for ω-carboxyl group.

SUMMARY OF THE INVENTION

The present inventors have completed the present invention as a result of diligent studies to eliminate the problems of the conventional methods and to develop new protecting groups which, participating in no undesirable side reactions, are strong in selectivity and hence can take the place of the conventional protecting groups for carboxyl group.

In summary, the present invention relates, in one aspect thereof, to a method of synthesizing peptides containing straight-chain amino acid having ω-carboxyl group and/or ω-carboxyl group and up to seven carbon atoms and, in another aspect, to aspartic acid derivatives and their salts. The method of this invention is characterized by the steps of using 2-adamantyl group in peptide condensation to protect ω-carboxyl group and/or ω-carboxyl group of a starting compound containing these groups and of thereafter removing the protecting group with an acid such as methanesulfonic acid. The compounds of the present invention, on the other hand, are characterized by the general formula

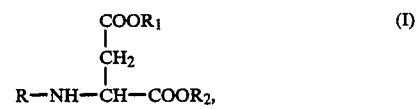

where either $R_1$ or $R_2$ is 2-adamantyl group, the other of $R_1$ and $R_2$ is hydrogen or a protecting group other than 2-adamantyl group, R is hydrogen or a protecting group of α-amino group, and its stereochemical configuration may be L, D or DL.

BRIEF DESCRIPTION OF THE DRAWING

The accompanying drawing, which is incorporated in and forms a part of the specification, is a flowchart of processes for peptide synthesis embodying the present invention and, together with the following detailed description, serves to explain the principles of the invention.

DETAILED DESCRIPTION OF THE INVENTION

With reference to the summary of the present invention described briefly above, 2-adamantanol is usually used as the 2-adamantyl group. A method of synthesizing 2-adamantanol is described below in Reference Example 1. The amino acid of the present invention having ω-carboxyl group and/or ω-carboxyl group protected by 2-adamantyl group can be synthesized by protecting α-amino group with any known protecting group and by the condensation reaction between ω-carboxyl group and/or ω-carboxyl group and 2-adamantanol by Tam's method (Tam, et al., Tetrahedron Letters, Vol. 42, pp. 4033–4036 (1979)). In the case of α,ω-dicarboxyl-amino acid having ω-carboxyl group; if it is desired to protect only either one of ω-carboxyl group or α-carboxyl group with 2-adamantyl group, it is preferable to introduce 2-adamantyl group after either ω-carboxyl group or ω-carboxyl group is protected by any protecting group of a known kind. The condensation reaction can take place at −20° C.–40° C. in a solvent (such as dichloromethane, chloroform, carbon tetrachloride, dioxane, tetrahydrofuran, dimethylformamide, diethylformamide, dimethylacetoamide, ethyl acetate, butyl acetate, N-methylpyrrolidone and hexamethylene phosphorictriamide) by using a condensation reagent (such as dichlorohexylcarbodiimide, diisopropylcarbodiimide, carbonyldiimidazole, 1-ethyl-3-(3-dimethylaminopropyl) carbodiimide and their salts). Examples of protecting group for α-amino group include such known groups as benzyloxycarbonyl group, p-nitrobenzyloxycarbonyl group, p-methoxybenzyloxycarbonyl group, p-chlorobenzyloxycarbonyl group, t-butoxycarbonyl group, t-amyloxycarbonyl group, 9-fluorenylmethoxycarbonyl group, isonicotinyloxycarbonyl group, trichloroacetyl group, trifluoroacetyl group, trichloroethoxycarbonyl group and 2-(trimethylsilyl)-ethoxycarbonyl group. Examples of protecting group for the other group ($\omega$-carboxyl group or $\omega$-carboxyl group) not protected by the aforementioned 2-adamantyl group include such known groups as benzyl group, t-butyl group, trityl group, trichloroethyl group, chlorobenzyl group, paranitrobenzyl group, paramethoxybenzyl group, methyl group, ethyl group, isopropyl group, diphenylmethyl and 2,4,6-trimethylbenzyl group. Amino acids of the present invention thus obtained, having $\omega$-carboxyl group and/or $\alpha$-carboxyl group protected by 2-adamantyl group, can be used extremely advantageously in the synthesis of peptides containing them by first forming a salt of carboxyl group such as dicyclohexylamine, cyclohexylamine, t-butylamine, sodium, sodium carbonate, sodium hydrogencarbonate, potassium carbonate, potassium hydrogencarbonate, magnesium oxide, triethylamine, diethylamine, quinoline and pyrimidine or a salt of amino group with hydrochloric acid, sulfuric acid, phosphoric acid, acetic acid, citric acid, tartaric acid, malic acid, succinic acid, glycolic acid, lactic acid, oxalic acid, malonic acid, etc. For the synthesis, any of known methods may be used such as those described by E. Schroeder and K. Luebke in "The Peptides" (Academic Press, Inc., New York, 1965), E. Gross and J. Meinhofer "The Peptides" Vols. 1 and 2 (Academic Press, Inc., New York, 1979 and 1980) and H. Yajima in "Lectures On Experiments In Biochemistry 1, Chemistry Of Proteins IV, Peptide Synthesis" (Tokyo Kagaku Dojin, 1977). More in detail, examples of the method of synthesis include the azide method, the chloride method, the acid anhydride method, the mixed acid anhydride method, the DCC method, the active ester method, the EEDQ method, the method of using Woodward reagent K, the carbonyldiimidazole method, the oxidation-reduction method and the DCC/HOBT method. After the step of peptide condensation, the protecting group of the present invention is removed with an acid. Although a known method of acid treatment such as the trifluoromethanesulfonic acid method, the hydrogen fluoride method and the trimethylsilyl-trifluoromethanesulfonic acid method can be used for this purpose, the removal can be easily effected also with a milder acid such as methanesulfonic acid. The quantity of the acid required to be used for deprotection is only that amount which is sufficient for removing the protecting group. More in detail, it is desirable to use $1-10^5$ equivalents, or preferably $1-10^3$, for one equivalent of 2-adamantyl group. Temperature should be $-40°$ C.-$100°$ C., or preferably $-20°$ C,-$60°$ C. If methanesulfonic acid is used, it may be used singly or in combination with trifluoroacetic acid serving as solvent.

The most common examples of amino acid of the present invention having $\omega$-carboxyl group are aspartic acid and glutamic acid and many peptides containing them are found among the naturally-occurring physiologically active peptides such as the insulin-releasing tetrapeptides which were synthesized by a method of the present invention (as described below as Reference and Model Examples) and by which usefulness of the aspartic acid derivatives and the method of peptide synthesis according to the present invention has been established. In addition, MSH (melanocyte-stimulating hormone), ACTH, insulin, glucagon, glycentin, secretin, gastrin, thyrocalcitonin, neurophysin, $\beta$-LPH (lipotropic hormone), $\beta$-endorphin growth hormone, prolactin, thyrotropic hormone, follicle-stimulating hormone, interstitial cell-stimulating hormone, eredoicin, physaraemin, uperolein, casinin, $\delta$-sleep-inducing peptide, urogastrone, epithelial cell growth factors, nerve growth factors, fibroblast growth factors, statelin, parotin, calcitonin, parathyroid hormone, thymosin $\alpha_1$, thymosin $\beta_4$, thymopoietin II, ubiquitin, somatomedin, relaxin, pancreatic polypeptide, cholecystokinin-pancreozymin, pathoactive intestinal polypeptide, gastric inhibitory polypeptide, motilin, PHI, PYY, hCS, hPL, angiotensin and their active fragments can also be synthesized by a method of the present invention. Stereoisomerism of the amino acid may be L, D or DL if there is an optically active substance.

Straight-chain amino acids thus obtained having $\omega$-carboxyl group and/or $\alpha$-carboxyl group protected by 2-adamantyl group and seven or less carbon atoms as well as peptides containing such amino acid are new compounds and the method of the present invention can be used advantageously for peptide synthesis not only by a liquid-phase method but also by a solid-phase method.

In that follows, the present invention will be explained more in detail by way of examples but they are not intended to limit the scope of the present invention. The processes of peptide synthesis according to the present invention are summarized in the accompanying drawing. Abbreviations based on the IUPAC-IUB Commission On Biological Nomenclature as well as those commonly accepted by persons in the art will be used in these examples. Some of these abbreviations are summarized in Table I. Angles of rotation presented below were all measured by using the sodium D-line.

TABLE 1

| Boc: | t-butoxycarbonyl |
|---|---|
| Z: | benzyloxycarbonyl |
| 2-Ad: | 2-adamantyl |
| O-2-Ad: | 2-adamantyl ester |
| ONp: | paranitrophenyl ester |
| OBzl: | benzyl ester |
| HOSu: | N-hydroxysuccinimide |
| OSu: | N-hydroxysuccinimide ester |
| DCC: | dicyclohexylcarbodiimide |
| TFA: | trifluoroacetic acid |
| MSA: | methanesulfonic acid |
| TFMSA: | trifluoromethanesulfonic acid |
| TMSOTf: | trimethylsilyltrifluoromethanesulfonate |
| DMAP: | 4-dimethylaminopyridine |
| DMF: | dimethylformamide |
| Et$_3$N: | triethylamine |
| Glp: | pyroglutamic acid |
| Glu: | glumatic acid |
| Glu(OBzl): | glutamic acid-$\gamma$-benzyl ester |
| Asp: | aspartic acid |
| Asp-OBzl: | aspartic acid-$\alpha$-benzyl ester |
| Asp(OBzl) | aspartic acid-$\beta$-benzyl ester |
| Asp(O-2-Ad): | aspartic acid-$\beta$-2-adamantyl ester |
| Asp(OcHex): | aspartic acid-$\beta$-cyclohexyl ester |
| Gly: | glycine |
| Ser: | serine |
| Ser(Bzl): | serinebenzyl ester |
| Ser-OMe: | serinemethyl ester |
| Thr: | threonin |

REFERENCE EXAMPLE b 1

Synthesis of 2-adamantanol

Dissolved in 300 ml of ether was 30.0 g (0.20 mole) of 2-adamantanon and 7.3 g (0.19 mole) of lithium aluminum hydride suspended in 150 ml of ether was added. The mixture was stirred for 2 hours at room temperature (25° C). After 2-N-HCl was added to make it acidic and the water layer was extracted with dichloromethane, it was washed together with the ether layer and dried with sodium sulfate. The solvent was removed by evaporation at reduced pressure to obtain white powder. The test results were as follows:

Yield 30 1 g (quantitative analysis)
Melting Point: 296°–299° C.

MODEL EXAMPLE 1

Synthesis of Boc-Asp(O-2-Ad)-OBzl

Dissolved in 50 ml of dichloromethane and cooled with ice were 5.0 g (14 mmole) of Boc-Asp-OBzl, 2.34 g (15.4 mmole) of 2-adamantanol and 171 mg (1.4 mmole) of DMAP. After 3.18 g (15.4 mmole) of DCC was added, the mixture was stirred overnight at 4° C. DCC-urea which was generated was removed by filtration and the filtrate was removed by evaporation at reduced pressure to obtain an oily substance. After 2 ml of ethanol was added for crystallization, it was cooled, filtered and washed with cold ethanol. The residue was recrystallized from ethanol. The test results were as follows:

Yield: 5.01 g (78.1%)
Melting Point: 74°–75° C.
Angle of Rotation: $[\alpha]_D^{23} + 8.3°$ (C=1.0, chloroform)
$Rf_1$ (chloroform:methanol:acetic acid=90:8:2)=0.92
$Rf_2$ (chloroform:ether=4:1)=0.81
Elementary Analysis (as $C_{26}H_{35}O_6N$): Calculated Values: C=68.3; H=7.71; N=3.06.
Experimental Values: C=68.2; H=7.75; N=3.32.

MODEL EXAMPLE 2

Synthesis of Boc-Asp(O-2-Ad)-OH

After 1.34 g (2.93 mmole) of Boc-Asp(0-2-Ad)-OBzl was dissolved in 30 ml of methanol, palladium black was used as catalyst for catalytic reduction according to a known method. The catalyst was removed by filtration and the filtrate was concentrated at reduced pressure. After a small amount of ethanol was added to the remaining condensed liquid, it was left quietly. Deposited crystals were collected and ethanol and water were used for recrystallization. The test results were as follows:

Yield: 880 mg (81.7%)
Melting Point: 111°–114° C.
Angle of Rotation: $[\alpha]_D^{29} + 21.8°$ (C=1.2, chloroform)
$Rf_1$=0.85, $Rf_3$ (chloroform:methanol:water=200:75:13)=0.96
Elementary Analysis (as $C_{19}H_{29}O_6N$):
Calculated Values: C=62.1; H=7.96; N=3.81.
Experimental Values: C=62.0; H=8.03; N=3.66.

MODEL EXAMPLE 3

Dissolved in 60 ml of ethyl acetate was 5 g (13.6 mmole) of Boc-Asp(O-2-Ad)-OH and 1.72 g (15.0 mmole) of HOSu was added. After 4 ml of DMF was added and the mixture was cooled with ice, 3.09 g (15.0 mmole) of DCC was added and the mixture was stirred overnight. DCC-urea which was generated was removed by filtration and the filtrate was hardened at reduced pressure. Petroleum benzene was added to the residue to obtain crystals. The residue was recrystallized from ethanol. The test results were as follows:

Yield: 4.90 g (77.5%)
Melting Point: 130°–132° C.
Angle Rotation: $[\alpha]_D^{29} - 7.8°$ (C=0.5, chloroform)
$Rf_1$=0.85
Elementary Analysis (as $C_{23}H_{32}O_8N_2$):
Calculated Values: C=59.47; H=6.94; N=6.03.
Experimental Values: C=59.32; H=6.91; N=5.97.

MODEL EXAMPLE 4

Synthesis of Z-Aso(O-2-Ad)-OBzl

Dissolved in 50 ml of dichloromethane were 2.0 g (5.6 mmole) of Z-Asp-OBzl, 0.85 g (5.6 mmole) of 2-adamantanol and 0.073 g (0.6 mmole) of DMAP and after 1.24 g (6.0 mmole) of DCC was added while the mixture was cooled with ice, it was stirred overnight. DCC-urea which was deposited was removed by filtration and after the residue was washed with 5%-sodium hydrogencarbonate while being cooled with ice, it was dried with magnesium sulfate. The solvent was removed by evaporation and an oily substance was obtained. This oily substance was dissolved in acetonitrile and the crystals which formed at low temperature were collected by filtration. Recrystallization was obtained from acetonitrile. The test results were as follows:

Yield: 2.56 g (93.1%)
Melting Point: 178°–182° C.
Angle Rotation: $[\alpha]_D^{27} + 9.4°$ (C=1 8, chloroform)
$Rf_1$=0.94, $Rf_2$=0.89
Elementary Analysis (as $C_{29}H_{33}O_6N$):
Calculated Values: C=70.85; H=6.77; N=2.85.
Experimental Values: C=70.55; H=6.84; N=3.12.

MODEL EXAMPLE 5

Synthesis of H-Aso(O-2-Ad)-OH

Dissolved in 10ml of ethanol was 160 mg (0.325 mmole) of Z-Asp(O-2-Ad)-OBzl and palladium black was used as catalyst for catalytic reduction according to a known method. The catalyst was removed by filtration and the filtrate was concentrated at reduced pressure to cause precipitation. The precipitate was obtained by filtration and recrystallized from ethanol and ether. The test results were as follows:

Yield: 37.7 mg (42.0%)
Melting Point: 218°–221° C.
Angle of Rotation: $[\alpha]_D^{29} - 11\ 5°$ (C=0.5, methanol)
$Rf_4$ (upper layer of (n-butanol:acetic acid:water=4:1:5))=0.47
$Rf_3$=6.60
Elementary Analysis (as $C_{14}H_{21}O_4N \cdot 1/2H_2O$):
Calculated Values: C=60.85; H=8.03; N=5.07.
Experimental Values: C=60.83; H=7.88; N=5.02.

MODEL EXAMPLE 6

Synthesis of Boc-Aso(O-2-Ad)-Gly-OBzl

After 1.35 g (4.0 mmole) of paratoluenesulfonate of H-Gly-OBzl was added to 20 ml of ethyl acetate, 0.21 g (2.0 mmole) of sodium carbonate was added and the mixture was stirred. After five minutes, the ethyl acetate layer was washed with water and dried with sodium sulfate. After 3 ml of DMF and 1.86 g (4.0 mmole) of Boc-Glu(OBzl)-Asp(O-2-Ad)-Gly-OBzl were added, 0.76 g (1.5 mmole) of a DMF solution containing 20% of triethylamine was dropped over a period of ten minutes and the mixture was stirred overnight. After ethyl acetate was removed by evaporation, the residue was refined by silica gel chromatography (solvent:- chloroform) and an oily substance was obtained. The test results were as follows:

Yield: 1.39 g (75.2%)
Angle of Rotation: $[\alpha]_D^{26} - 11.8°$ (C=1.0, methanol)
$Rf_5$ (chloroform)=0.17, $Rf_2$ 0.72
Elementary Analysis (as $C_{28}H_{38}N_2O_7$):
Calculated Values: C=65.4; H=7.44; N=5.44.
Experimental Values: C=65.6; H=7.69; N=5.28.

MODEL EXAMPLE 7

Synthesis of Boc-Glu(OBzl)-Asp(O-2-Ad)-Glv-OBzl

After 422 mg (0.82 mmole) of Boc-Asp(O-2-Ad)-Gly-OBzl was dissolved in 0.93 ml (8.2 mmole) of TFA containing 0.18 ml (1.64 mmole) of anisole, it was stirred for thirty minutes at 0° C. and then at room temperature (20° C.). TFA was removed by evaporation and after the residue was vacuum-dried over potassium hydroxide, 376 mg (0.82 mmole) of Boc-Glu(OBzl)-ONp was added and dissolved by adding 10 ml of ethyl acetate. To this was added 1.13 ml (1.64 mmole) of ethyl acetate containing 20% of triethylamine and the mixture was stirred for one day at room temperature. Added to this solution was 10 ml of ethyl acetate and it was washed sequentially with 5% sodium carbonate, 10% citric acid and water. It was then dried with sodium sulfate and evaporated. The remaining oily substance was refined with silica gel chromatography (solvent:chloroform). A colorless oily substance was obtained. The test results were as follows:

Yield: 450 mg (74.8%)
Angle of Rotation: $[\alpha]_D^{26} - 19.0°$ (C=0.5, methanol)
$Rf_1$=0.88, $Rf_2$=0.38
Elementary Analysis (as $C_{40}H_{51}N_3O_{10}$):
Calculated Values: C=65.5; H=7.01; N=5.73.
Experimental Values: C=65.3; H=6.90; N=5.55.

MODEL EXAMPLE 8

Synthesis of Boc-Glp-Glu(OBzl)-Aso(O-2-Ad)-Glv-OBzl

After 380 mg (0.52 mmole) of Boc-Glu(OBzl)Asp(O-2-Ad)-Gly-OBzl was added to 0.6 ml (5.26 mmole) of TFA containing 0.2 ml (1.85 mmole) of anisole, it was stirred for thirty minutes at 0° C. and then for one hour at room temperature (20° C). After petroleum benzene was added and the mixture was cooled with ice, the precipitation which resulted was collected by filtration and vacuum-dried over potassium hydroxide. After 190 mg (0.53 mmole) of Z-Glp-OSu and 10 ml of ethyl acetate were added to the powder thus obtained and the mixture was stirred, 1.10 ml (1.60 mmole) of ethyl acetate containing 20% of triethylamine was added and the mixture was stirred overnight at room temperature. The solvent was removed by evaporation and ether was added to the residue to obtain crystals which were filtered and washed with ethanol. Recrystallization was obtained from ethyl acetate and ether. The test results were as follows:

Yield: 251 mg (55.1%)
Melting Point: 148°-150° C.
Angle of Rotation: $[\alpha]_D^{29} - 39.2°$ (C=0.5, methanol)
$Rf_1$ =0.63, $Rf_3$=0.45
Elementary Analysis (as $C_{48}H_{54}N_4O_{12}$):
Calculated Values: C=65.6; H=6.19; N=6.37.
Experimental Values: C=65.5; H=6.22; N=6.37.

MODEL EXAMPLE 9

Synthesis of H-Glo-Glu-Asp-Gly-OH (insulin-releasing tetrapeptide)

After 1 ml (13.1 mmole) of MSA containing 0.15 ml of anisole was added to 90 mg (0.1 mmole) of Z-Glp-Glu(OBzl)-Asp(O-2-Ad)-Gly-OBzl, the mixture was stirred for thirty minutes at 0° C. and further for one hour at room temperature (20° C.). Ether was added to the liquid to solidify it and the solid substance thus obtained was dissolved in water and washed with ether. The water layer was frozen and dried to obtain powder. The test results were as follows:

Yield: 53 mg (100%)
Angle of Rotation: $[\alpha]_D^{23} - 42.8°$ (C=0.5, water)
$Rf_6$ (n-butanol:acetic acid:pylidine:water=4:1:1:2)=0.27,
$Rf_7$ (n-butanol:acetic acid:pylidine:water=1:1:1:1) =0.50

MODEL EXAMPLE 10

Synthesis of Boc-Asp(O-2-Ad)-Ser-Ser-Thr-Ser-OMe

After 90 mg (0.193 mmole) of Boc-Asp(O-2-Ad)-OSu and 60 mg (0.152 mmole) of H-Ser-Ser-Thr-Ser-OMe were dissolved in 2 ml of DMF and 0.1 ml (0.143 mmole) of DMF containing 20% of triethylamine, the mixture was stirred for twelve hours at room temperature (20° C.). The solvent was removed by evaporation at reduced pressure and 8 ml of ethyl acetate was added to the residue to obtain precipitation. The precipitate was collected by filtration, washed sequentially by water and ether and dried at reduced pressure. Powder thus obtained was dissolved in 1 ml of DMF and refined by reverse phase chromatography by the method of continuous concentration gradient elution with a YMC D-ODS-5 column and using water and acetonitrile as a solvent. The test results were as follows:

Yield: 66.3 mg (56.6%)
Melting Point: 191°-196° C.
Angle of Rotation $[\alpha]_D^{25} - 2.6°$ (C=0.2, DMF)
$Rf_4$=0.82
Elementary Analysis (as $C_{33}H_{53}N_5O_{14}$):
Calculated Values: C=53.3; H=7.18; N=9.42.
Experimental Values: C=53.0: H=7.21: N=9.14.

REFERENCE EXAMPLE 2

Synthesis of Boc-Asp(OcHex)-Ser-Ser-Thr-Ser-OMe

Use was made of 80 mg (0.193 mmole) of Boc-Asp(O-cHex)-OSu and the desired compound was obtained by a similar method to Model Example 10. The test results were as follows:

Yield: 50.9 mg (49.5%)
Angle of Rotation: $[\alpha]_D^{25} - 3.8°$ (C=0.2, DMF)
$Rf_4$=0.82
Elementary Analysis (as $C_{29}H_{49}N_5O_{14} - 3/2H_2O$):
Calculated Values: C=48.5; H=7.29; N=9.74.
Experimental Values: C=48.2; H=6.95; N=9.76.

TEST EXAMPLE 1

Under each of the following eight conditions, 20 μmole of H-Asp(O-2-Ad)-OH was processed for 5 minutes, 60 minutes and 120 minutes to produce three samples (that is, a total of 3×8=24 samples). After each of these samples was adjusted to pH=2 with $IN-Na_2CO_3$ or 1N-HCl, water was added to make its volume to 5 ml for analysis of amino acid and the yield of aspartic acid was measured:

(1) 2 ml (100 equivalents) of 1 N-HCl
(2) 0.5 ml (200 equivalents) of 7 N-HCl
(3) 0.5 ml (300 equivalents) of TFA
(4) 0.5 ml (400 equivalents) of MSA
(5) 0.5 ml of TFA containing 0.1 ml (50 equivalents) of TFMSA and 0.01 ml of thioanisole (referred as TFMSA/TFA)
(6) 0.5 ml of TFA containing 0.1 ml (30 equivalents) of TMSOTf and 0.01 ml of thioanisole (referred as TMSOTf/TFA)
(7) 1 ml of TFA containing 0.01 ml of anisole and 0.1 ml (250 equivalents) of HF (referred as HF/TFA) (8) 2 ml (70 equivalents) of dioxane containing 10% of Et3N (referred as Et3N/dioxane)

For the sake of comparison, (9) 0.5 ml (400 equivalents) of MSA was added to 20 μmole of H-Asp(OcHex)-OH at room temperature (20° C.) and measurements were similarly made thereof. The test results are shown together in Table 2

TABLE 2

| Sample | Condition | Yield of aspartic acid (%) after | | |
|---|---|---|---|---|
| | | 5 min | 60 min | 120 min |
| H-Asp(O-2-Ad)-OH | (1) | 100 | 0 | 1 |
| | (2) | 0 | 1 | 1 |
| | (3) | 0 | 0 | 0 |
| | (4) | 100 | | |
| | (5) | 100 | | |
| | (6) | 100 | | |
| | (7) | 100 | | |
| | (8) | 0 | 0 | 0 |
| H-Asp-(OcHex)-OH | (9) | 74 | 85 | 86 |

Apparatus for amino acid analysis: Model K-101AS produced by Kyowa Seimitsu, Inc.

TEST EXAMPLE 2

Condensation of Boc-Asp(OR)-OSu (where OR represents O-2-Ad, OcHex or OBzl) and H-Ser-Ser-Thr-Ser-OMe was carried out in the same way as in Model Example 10 except temperature at the time of condensation was 30° C. and 20 μl each of the following three liquid reactants (after twelve hours) was taken: (1) reaction using Boc-Asp(O-1-Ad)-OSu (2) reaction using Boc-Asp(OcHex)-OSu (3) reaction using Boc-Asp(OBzl)-OSu After each was diluted with 200 μl of acetonitrile, 10 μl thereof was used for high-speed liquid chromatography for quantitative analysis of the target compound Boc-Asp(OR)-Ser-Ser-Thr-Ser-OMe and by-product succinimide and their yields were calculated. The test results are shown in Table 3. The conditions of the measurements were as follows:

Column: YMC-PACK R-ODS-5 (4.6x250 mm)
Detection Wavelength: 220 nm
Flow Rate: 1 ml/minute
Solvent: continuous step-wise variation in concentration according to A/B=85/15-(30 minutes)-30/70-(10 minutes)-85/15 where A represents water containing 0.1% of TFA and B represents acetonitrile containing 0.1% of TFA.

TABLE 3

Yields of products from condensation reactions (at 30° C.) of Boc-Asp(OR)-OSu and H-Ser-Ser-Thr-Ser-OMe

| | Yield (%) | |
|---|---|---|
| R | Target Product | By-Product succinimide |
| -2-Ad | 81 | 5 |
| cHex | 69 | 7 |
| Bzl | 0*1 | 53 |

High-speed liquid chromatograph: Waters ALC-206 Quantitative analysis done directly by connecting Waters M-740 integrater.
*1: This entry is given because it is known (Okada, et al., Chem. Pharm. Bull., Vol 35, pp. 468–478 (1987)) that there is no generation of Boc-Asp(OBzl)-Ser-Ser-Thr-Ser-OMe if Boc-Asp(OBzl)-OSu is used.

In summary, the 2-adamantyl group on the amino acid derivatives of the present invention with their ω-carboxyl group and/or α-carboxyl group protected by 2-adamantyl group is stable against treatment with trifluoroacetic acid as shown in Table 2 but can be removed quickly when treated with methanesulfonic acid which is milder than trimethylsilyl, trifluoromethanesulfonate or hydrogen fluoride. Because of this desirable characteristic, peptides can now be synthesized by using α-amino protecting group which can be removed with trifluoroacetic acid to extend the peptide chain and methanesulfonic acid for the final deprotection. Thus, since a new method of deprotection by the combination of trifluoroacetic acid and methanesulfonic acid is now available, peptide synthesis can be effected by a simpler procedure than previously possible. Since the conditions on the final deprotection are now less stringent, side reactions are less likely to take place and desired peptides can be obtained without damaging the remaining groups extensively. In fact, the desired peptides can be obtained with a high yield as shown in Model Example 9. With the method of the present invention, furthermore, expensive special apparatus for handling hydrogen fluoride are no longer necessary and since no excessively corrosive liquids like trifluoromethanesulfonic acid are involved, no particular measures are required for safety and deprotection can be effected very easily. In short, the method of the present invention is industrially very advantageous. The method of the present invention can easily take the place of the conventional protection methods using hydrogen fluoride, trifluoromethanesulfonic acid or trimethylsyliltrifluoromethanesulfonate.

If conventional protecting groups are compared, the cyclohexyl group, for example, shows no variations with time after five minutes and there is no quantitative removal. This clearly shows that adamantyl group is extremely effective as protecting group with superior selectivity characteristic and can be used for the synthesis of desired peptides with a high yield. If peptide synthesis is attempted by using conventional protecting groups, Table 3 shows that the desired peptides could not be obtained at all with benzyl group although a large quantity of byproduct succinimide was obtained. With the use of 2-adamantyl group according to the present invention, by contrast, the yield of by-product is extremely small compared to the conventional method and the yield of the target compound is clearly higher.

What is claimed is:
1. An aspartic acid derivative which is N-α-t-butoxycarbonyl-aspartic acid-β-2-admantyl ester-α-benzyl ester.
2. An aspartic acid derivative which is N-α-t-butoxycarbonyl-aspartic acid-β-2-adamantyl ester.
3. An aspartic acid derivative which is benzyloxycarbonyl-aspartic acid-β-2-adamantyl ester-α-benzyl ester.
4. An aspartic acid derivative which is aspartic acid-β-2-admantyl ester.

* * * * *